(12) United States Patent
Busiashvili

(10) Patent No.: US 9,861,578 B1
(45) Date of Patent: Jan. 9, 2018

(54) SUBLINGUAL DOSIMETRIC DRIP CAGED BALL VALVE DEVICE

(71) Applicant: Yuri Issac Busiashvili, Pacific Palisades, CA (US)

(72) Inventor: Yuri Issac Busiashvili, Pacific Palisades, CA (US)

( * ) Notice: Subject to any disclaimer, the term of this patent is extended or adjusted under 35 U.S.C. 154(b) by 0 days.

(21) Appl. No.: 15/592,487

(22) Filed: May 11, 2017

(51) Int. Cl.
*A61K 9/00* (2006.01)
*A61J 1/22* (2006.01)
*A61M 15/00* (2006.01)

(52) U.S. Cl.
CPC ............ *A61K 9/006* (2013.01); *A61J 1/22* (2013.01); *A61M 15/0035* (2014.02)

(58) Field of Classification Search
CPC ....... A61K 9/006; A61J 1/22; A61M 15/0035; A61M 3/02; A61M 3/0279; A61M 5/282; A61M 35/00; A61M 35/003; A61M 35/006; A61M 5/40; A61M 5/1685; A61M 16/165; A61M 5/16877; A61M 1/005; A61M 2210/0625; A61M 39/00
See application file for complete search history.

(56) References Cited

U.S. PATENT DOCUMENTS

| 5,123,915 | A | | 6/1992 | Miller et al. |
| 5,263,475 | A | * | 11/1993 | Altermatt .......... A61M 15/0065 128/203.15 |
| 5,529,059 | A | * | 6/1996 | Armstrong ........ A61M 15/0028 128/203.12 |
| 7,089,934 | B2 | | 8/2006 | Stanforth et al. |
| 8,361,497 | B2 | | 1/2013 | Miller |
| 9,114,090 | B1 | | 5/2015 | Busiashvili |
| 9,205,248 | B2 | * | 12/2015 | Wu ........................ A61J 1/2096 |
| 9,615,997 | B2 | * | 4/2017 | Fangrow ................ A61J 1/2089 |
| 2013/0327327 | A1 | * | 12/2013 | Edwards ........... A61M 15/0028 128/203.11 |

* cited by examiner

*Primary Examiner* — Nathan R Price
*Assistant Examiner* — Melissa A Snyder
(74) *Attorney, Agent, or Firm* — Ralph D Chabot

(57) ABSTRACT

A device for self-administration of fractional amounts of a total volume dose of liquid medicament supplied from a capsule over a period of time for delivery to the sublingual area of a patient. The device contains an inner chamber and a track within which confines a moveable ball. The space between the chamber wall and track permits liquid medication from the capsule to flow past the ball and be available for discharge through an exit port when the ball is not seated upon the exit port.

12 Claims, 2 Drawing Sheets

SUBLINGUAL DOSIMETRIC DRIP CAGED BALL VALVE DEVICE

BACKGROUND OF THE INVENTION

Oral delivery of medications is one of the most frequent techniques utilized for delivering medication to the body. One of the most popular delivery mechanisms is the capsule. The background of U.S. Pat. No. 8,361,497 issued to Miller provides a detailed description into the history and present techniques for capsule manufacture and is hereby incorporated by reference.

Capsules containing medication for oral intake are usually swallowed for delivery of the medication to the stomach, where the capsule dissolves within 20 to 30 minutes and the medication is absorbed into the bloodstream.

With respect to capsular delivery of liquid medication such as Nfedipine for urgent cardiac conditions, a 20 to 30 minute wait time until absorption into the blood stream is not acceptable for particularly acute cardiac emergencies.

One example of a method of sublingual delivery of liquid medication contained in a capsule is U.S. Pat. No. 9,114,090 issued to Busiashvili which describes a capsular design and medication discharge from the capsule onto the sublingual area of a patient.

Another example of a device for oral delivery of liquid medication from a capsule is U.S. Pat. No. 5,123,915 issued to Miller et al. where a gelcap is punctured and the liquid contained within gravitates to a pierced nipple for subsequent oral delivery.

Another known delivery mechanism is by spray application of the medication onto the sublingual area. However, with spray application there is no limit upon the maximal amount of liquid medication delivered. In other words, a patient can repeatedly spray doses thus potentially leading to cardiovascular collapse.

For situations in which the patient or user is dealing with an acute condition such as an acute coronary insufficiency, a heart attack, hypertensive crisis or arrhythmia and for which a medication such as Nifedipine and Nitroglycerin is proscribed, the user is likely to take more medication than necessary or maximally allowed. It is this lack of limitations to the single dose which could lead to a precipitous drop of arterial blood pressure and could result in cardiovascular collapse, syncope or even death. Thus, it is submitted that the available medication doses for products such as Nifedipine and Nitroglycerin are of too high of a concentration for the treatment of some patients. A device to limit or delay the administration of the total volume dosage is believed to be a method of desired treatment.

SUMMARY OF THE INVENTION

Described herein is a device used for sublingual self-administration of liquid capsular medication in medical emergencies whereby a fraction of the total volume of liquid medication contained in the capsule or gelcap can be applied to the sublingual area at a given time. A common example of medication envisioned to be used by this device is Nifedipine or any other encapsulated liquid medication used for sublingual application in medical emergencies. Most preferably, the device will split the total volume dosage contained in the capsule into two or more fractions of the total volume dosage. This total capsular volume for sublingual administration is no larger than about 1.2 ml.

Accordingly, my invention describes a device which has a cylindrical cavity for partially receiving a capsule containing liquid medicament. Extending upward from the base wall of the cylindrical cavity is a hollow needle with a piercing tip facing into the cavity and the length of which is appropriately sized to puncture the capsular wall so that liquid medicament can enter the hollow needle. The liquid medicament, upon sufficient force applied to the non-punctured end of the capsule, will flow through the needle and an inlet into a chamber which houses a weighted displaceable ball. The side of the chamber opposite the inlet comprises an exit port which is configured to serve as a seat for the ball to prevent liquid flow through the exit port when the ball is seated. Downstream of the seat is a flow channel having a distal discharge nozzle from which liquid medicament will exit the device in a form of drop or drops for application to the sublingual area.

Medication contemplated for use by my device includes concentrated liquid medication forms such as Nifedipine. Because the medication is liquid, it is necessary to carefully select the material that will comprise the capsule wall so the liquid medication contained within cannot react and dissolve or mollify the capsule wall.

The intended purpose of my device is to deliver a fraction of the therapeutic amount sublingually which will alleviate the patient's acute condition in as short a time as thirty seconds and if the first volume fraction was insufficient to alleviate the medical condition in less than a minute, the remaining volume of medicament can be used as a subsequent volume fraction(s).

In a first preferred embodiment, the chamber includes a cage or track within which the ball can displace and at least one longitudinal space, offset from the track for liquid medicament to flow. By retaining the ball in a confined track, liquid medicament can flow past the ball in when the ball is not in the seated position. The size of the longitudinal space will be dependent upon the viscoscity of the medication. It is desired for the longitudinal space to be small in order for the liquid medication to travel from the capsule to the flow channel quickly.

In another embodiment, in addition to what has been previously described, the medication and device are sealed in a package and will also contain an audio device which will provide pre-recorded instructions when the package is opened.

In practice, to operate the device, the device is held in a horizontal position and a capsule is partially inserted into the cylindrical cavity of the device until the inserted end of the capsule contacts the piercing tip of the needle. While in this position, the ball is positioned somewhere on the track away from the seat. Next, a sufficient force is applied to the exposed portion of the capsule for the needle to puncture the capsular wall and displace the pierced end of the capsule into contact with the base wall of the cavity.

Next, while still preferably in the horizontal position, force is applied to the exposed end of the cavity, by the index finger or thumb to force some of the liquid medication from the capsule into the device. The lead portion of the liquid entering the device will be displaced to near the seat so that when the device is rotated to a vertical position, a fraction of the liquid medication is able to flow downstream of the seat and be available for sublingual application before the ball can seat. With the ball now seated when the device is in the vertical position, a fractional portion is also present upstream of the seated ball.

In a preferred embodiment, force does not have to be applied to have substantially all of the liquid medication transferred from the capsule to the device prior to sublingual application. The fraction of liquid medication located downstream of the seated ball will flow to the discharge nozzle which the user will position just above the sublingual area. The user will sense the medication dropping onto the sublingual area. Alternatively, the user may place their lips about the nozzle and suck the nozzle like the end of a straw.

It is possible this first fraction of liquid medication will be sufficient to treat the acute condition. However, if additional medication is determined by the user to be required, the user then rotates the device back to a horizontal position thereby unseating the ball, applying force again to the capsule to displace more liquid medication from the capsule into the device and then rotating the device back to the vertical position seating the ball again. This movement will position a second fraction of liquid medication downstream of the seated ball for sublingual application. This procedure can be repeated as necessary until no liquid medication remains.

DESCRIPTION OF THE PREFERRED EMBODIMENT

The figures provided herein are not drawn to scale and are provided for representational and instructional purposes.

Figure 1:
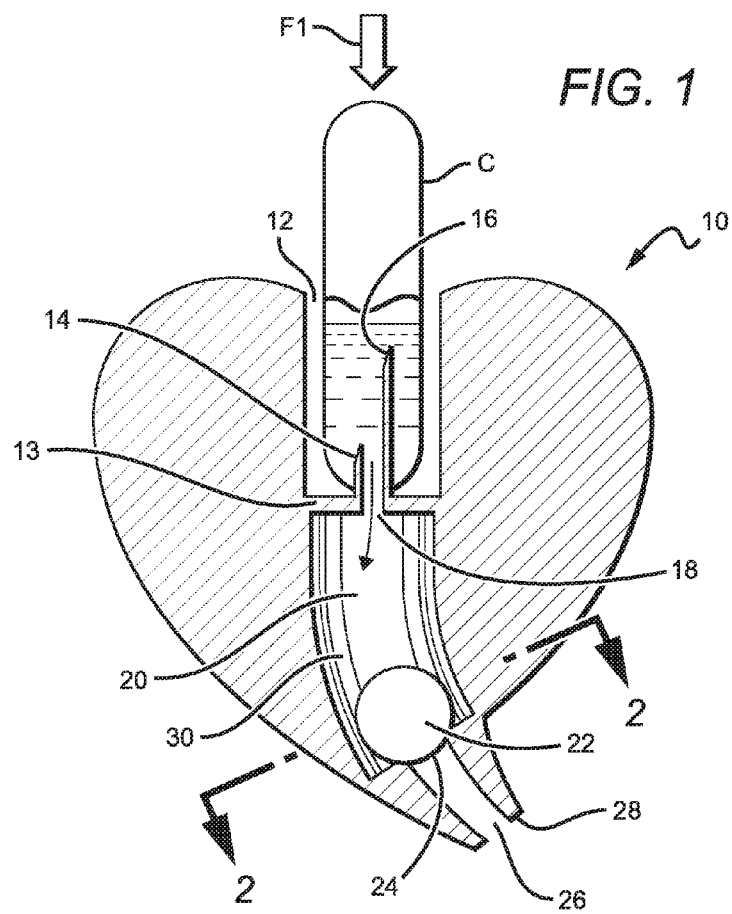
FIG. 1 is a cross sectional view of the device.

FIG. 1 illustrates a view of device 10. The exterior configuration is not limited to that disclosed but can be of any configuration suitable to be hand-held. Into the top surface of device 10 is a cylindrical cavity 12 having a base 13. Extending away from base 13 is a hollow needle 14 with a piercing tip 16 which faces into cavity 12. The cavity is suitably sized for receiving a capsule C containing liquid medicament LM and where the inserted end of the capsule can be punctured by applying an appropriate force F1 using a thumb or forefinger.

Figure 3:
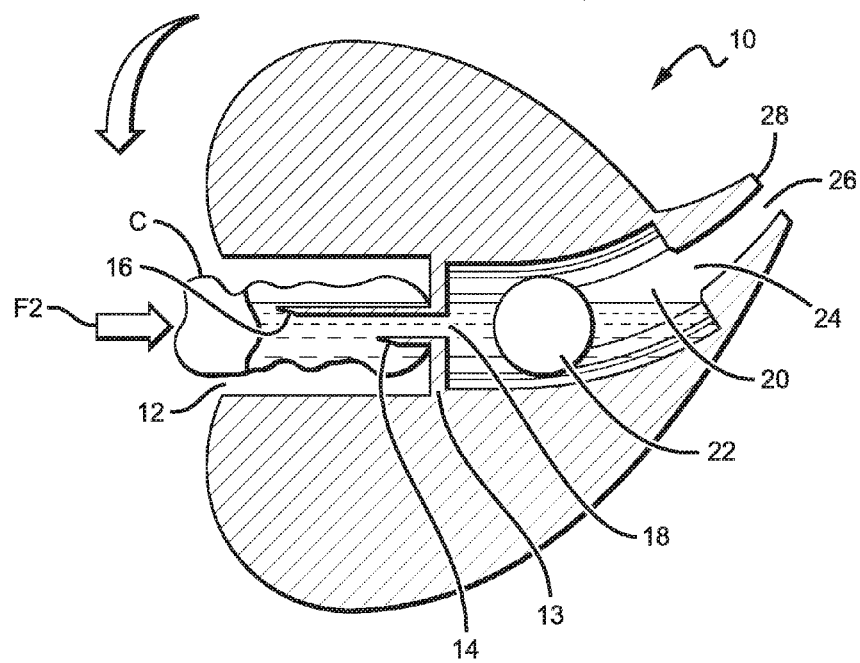
FIG. 3 illustrates the method of adding liquid medicament to the chamber by applying a force to the exposed end of the punctured capsule.

The length of needle 14 extending into cylindrical cavity 12 is of an appropriate length to puncture the capsular wall of capsule C and permit substantially all liquid medicament LM to enter needle 14 through piercing tip 16. As best illustrated in FIG. 3, upon sufficient force F2 applied to the non-punctured end of the capsule C, liquid medicament LM will be forced through needle 14 and inlet 18 into a chamber 20 which houses a weighted displaceable ball 22.

The side of the chamber opposite inlet 18 comprises an exit port 24 which is configured to serve as a seat for ball 22. When ball 22 is seated upon exit port 24, liquid present within chamber 20 is prevented from flowing downstream of the exit port. Downstream of exit port 24 is a flow channel 26 and a distal discharge nozzle 28 from which liquid medicament will exit the device for application to the sublingual area.

Figure 2:
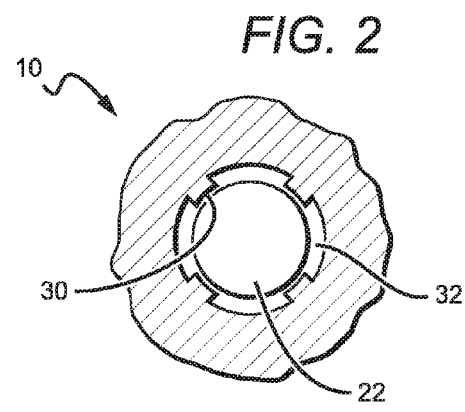
FIG. 2 is a view taken along line 2-2 of FIG. 1.

As illustrated in FIG. 2, chamber 20 includes a track within which ball 22 can displace. The track is defined by at least one inward elongated extension 30 of the chamber wall in a longitudinal orientation. A longitudinal space 32 exists for each inward extension. In a preferred embodiment illustrated in FIG. 2, there are 4 inward extensions 30 and corresponding spaces 32. Because ball 22 is limited to displacement within the track, liquid medicament LM present in chamber 20 can flow through exit port 24 when ball 22 is not seated upon exit port 24.

Figure 4:
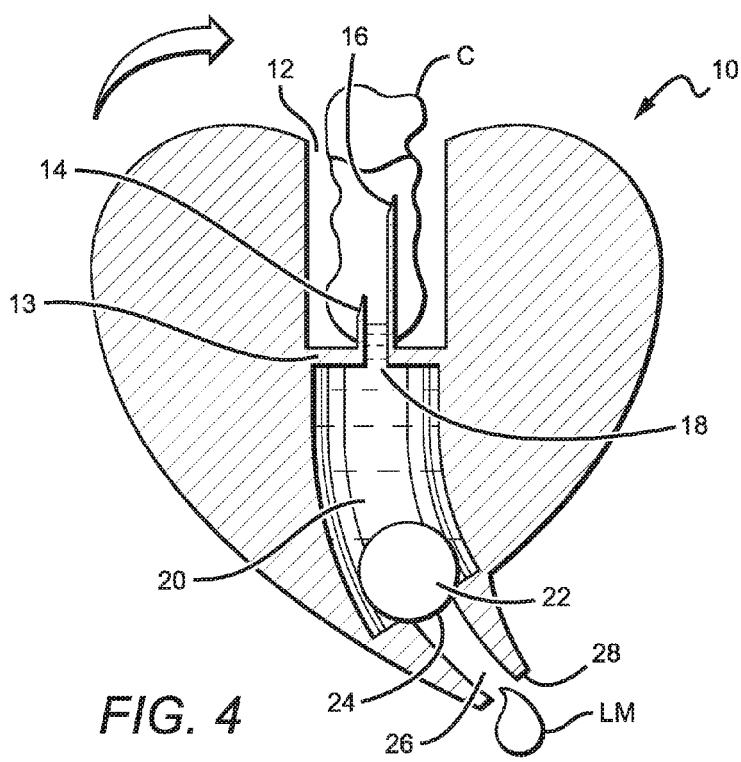
FIG. 4 illustrates the method for discharging liquid medicament from the device following rotation to a vertical position.

As device 10 is rotated, as shown in FIG. 4, to a substantially vertical position, ball 22 will seat upon exit port 24, and a fraction of the LM originally contained in the capsule will enter flow channel 26 before the ball can seat. The portion of the liquid medicament downstream of exit port 24 when ball 22 is seated is defined as a fraction of the total volume dosage and is available for sublingual application. It is to be understood that the term "substantially vertical position" means the position or orientation of device 10 in which ball 22 will seat upon exit port 24. Likewise, the term "substantially horizontal position" means the position or orientation of device 10 in which ball 22 is not seated upon exit port 24.

After the first fraction of the total volume dosage has been delivered to the sublingual area, the patient need only wait a matter of 30-60 seconds. If the cardiac event does not subside, device 10 can be rotated momentarily back from vertical to a horizontal position as shown in FIG. 3 to allow the user to again apply a force to capsule C discharging additional liquid medication into device 10. As device 10 is then rotated back to a vertical position as shown in FIG. 4, a second fraction of the total volume dosage is in the flow channel downstream of exit port 24 ready for sublingual application. This procedure can be repeated as necessary until no liquid medication remains.

I claim:

1. A device for the sublingual administration of a liquid medication which comprises:
    a cylindrical cavity having a base wall;
    a hollow needle having a piercing tip extending upward from the base wall; said cylindrical cavity sized to receive and align a capsule containing liquid medication for piercing of one end of the capsule by the piercing tip;
    said hollow needle having an outlet which communicates with a chamber having an exit port and a displaceable ball and where the interior area of the chamber about the exit port is configured to act as a seat and prohibit liquid medication to exit the chamber when the ball is positioned upon the exit port.

2. The device of claim 1 further comprising a discharge nozzle downstream of the exit port for positioning upon the sublingual area.

3. The device of claim 2 where the downstream flow path from the exit port to the discharge nozzle is arcuate.

4. The device of claim 1 where the chamber comprises at least one inward longitudinally elongated extension that defines a track within which the ball can displace.

5. The device of claim 4 where the ball is displaceable to a first position seated upon the exit port by orientating the device so that the needle is substantially in a vertical position.

6. The device of claim 4 where the ball is displaceable within the track to a second position where the ball is not in contact with the exit port by orientating the device so that the needle is in a substantially horizontal position.

7. A device for the sublingual administration of a liquid medication which comprises:
    a cylindrical cavity having a base wall;
    a hollow needle having a piercing tip extending upward from the base wall; said cylindrical cavity sized to receive and align a capsule containing liquid medication for piercing of one end of the capsule by the piercing tip;

said hollow needle having an outlet in which said outlet is the sole inlet into a chamber having an exit port and a displaceable ball and where the interior area of the chamber about the exit port is configured to act as a seat and prohibit liquid medication to exit the chamber when the ball is positioned upon the exit port.

8. The device of claim 1 further comprising a discharge nozzle downstream of the exit port for positioning upon the sublingual area.

9. The device of claim 8 where the downstream flow path from the exit port to the discharge nozzle is arcuate.

10. The device of claim 7 where the chamber comprises at least one inward longitudinally elongated extension that defines a track within which the ball can displace.

11. The device of claim 10 where the ball is displaceable to a first position seated upon the exit port by orientating the device so that the needle is substantially in a vertical position.

12. The device of claim 10 where the ball is displaceable within the track to a second position where the ball is not in contact with the exit port by orientating the device so that the needle is in a substantially horizontal position.

\* \* \* \* \*

UNITED STATES PATENT AND TRADEMARK OFFICE
CERTIFICATE OF CORRECTION

PATENT NO. : 9,861,578 B1  
APPLICATION NO. : 15/592487  
DATED : January 9, 2018  
INVENTOR(S) : Busiashvili Page 1 of 1

It is certified that error appears in the above-identified patent and that said Letters Patent is hereby corrected as shown below:

On the Title Page

The Applicant name should be corrected from "Yuri Issac Busiashvili" to "Yuri Busiashvili".

The Inventor name should be corrected from "Yuri Issac Busiashvili" to "Yuri Busiashvili".

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*